United States Patent [19]

Numa et al.

[11] 4,304,864

[45] Dec. 8, 1981

[54] LONG-CHAIN ACYL-COENZYME-A SYNTHETASE

[75] Inventors: Shosaku Numa, Kyoto; Kohei Hosaka, Maebashi, both of Japan; Masayoshi Mishina, Erlangen, Fed. Rep. of Germany; Takao Tanaka, Ibaragi; Tatsuyuki Kamiryo, Kyoto, both of Japan

[73] Assignee: Mitsubishi Chemical Industries, Limited, Tokyo, Japan

[21] Appl. No.: 80,218

[22] Filed: Oct. 1, 1979

[30] Foreign Application Priority Data

Sep. 29, 1978 [JP] Japan .................. 53-120118
Nov. 27, 1978 [JP] Japan .................. 53-146345

[51] Int. Cl.$^3$ .............................................. C12N 9/10
[52] U.S. Cl. .................................. 435/193; 435/814; 435/815
[58] Field of Search .................... 435/193, 814, 815

[56] References Cited

U.S. PATENT DOCUMENTS 3,907,642 9/1975 Richmond .................. 435/815 X
4,229,538 10/1980 Yamada et al. .................. 435/193

OTHER PUBLICATIONS

Estroumza et al., Chemical Abstracts vol. 72, 96873x (1970).
Ray et al., Chemical Abstracts vol. 86, 52028k (1977).
Kamiryo et al., Chemical Abstracts vol. 88, 34332s (1978).
Samuel et al., Eur. J. Biochem. vol. 12 (1970) 576–582.
Ray et al., Proc. Natl. Acad. Sci. vol. 73, No. 12, pp. 4374–4378, Dec. 1976.
Kamiryo et al., Proc. Natl. Acad. Sci. vol. 74, No. 11, pp. 4947–4950, Nov. 1977.

*Primary Examiner*—Lionel M. Shapiro
*Attorney, Agent, or Firm*—Oblon, Fisher, Spivak, McClelland & Maier

[57] ABSTRACT

There are disclosed an enzyme, long-chain acyl-coenzyme-A synthetase which is specific for fatty acids having 14 to 18 carbon atoms and a process for the purification of the enzyme which involves solubilizing the enzyme with a surfactant and subjecting the solubilized enzyme to affinity chromatography.

10 Claims, 5 Drawing Figures

LONG-CHAIN ACYL-COENZYME-A SYNTHETASE

BACKGROUND OF THE INVENTION

1. Field of the Invention

This invention relates to long-chain acyl-coenzyme-A synthetase (abbreviated throughout the specification and claims as acyl-CoA synthetase, EC. 6.2.1.3), and a process for the purification of the enzyme.

2. Description of the Prior Art

The acyl-CoA synthetase is an important enzyme participating in the first stage of oxidation of fatty acids in the living body and catalyzes the following reaction:

$$RCOOH + CoA + ATP \rightarrow RCOCoA + AMP + \text{Pyrophosphoric Acid} \quad (1)$$

(In the above formula (1), R represents a saturated or unsaturated alkyl.)

This enzyme is known to occur in the rat liver, various bacteria and yeasts, for example, Escherichia coli and bacilli. Heretofore, many attempts have been made to purify the enzyme, but none of them have been successful in isolating the enzyme as a pure preparation because of its tendency to bind to the membranes as well as its instability.

For example, D. Samuel et al in the European Journal of Biochemistry, Vol. 12, pages 576–582 (1970) made purification of acyl-CoA synthetase from Escherichia coli (hereinafter referred to as E. coli), but they failed to purify the enzyme as an entirely homogeneous protein, the purified product having a low specific activity per milligram of protein.

Purification of the long-chain acyl-CoA synthetase from microsomes of the rat liver was also attempted by J. Bar-Tana et al in the Biochemical Journal, Vol. 122, pages 353–362 (1971), but, the homogeneity of the purified enzyme was not sufficient from the electrophoretic data and the specific activity thereof was also low.

The inventors previously found in the course of their study on acyl-CoA synthetase from microorganisms that the enzyme included two distinct enzymes, acyl-CoA synthetases I and II wherein acyl-CoA synthetase I participated in the systems for direct incorporation of fatty acids into lipids and acyl-CoA synthetase II participated in the β-oxidation systems of fatty acids [Mishina et al, European Journal of Biochemistry, Vol. 82, pages 347–354 (1978)].

Among these, acyl-CoA synthetase is the enzyme which the present invention concerns. (In the following description, by the expression "the enzyme" is meant acyl-CoA synthetase I unless otherwise specified.)

Upon extensive investigation on the purification of longchain acyl-CoA synthetase I of microorganism origin, the inventors have succeeded in isolating the enzyme having a significantly high specific activity and homogeneous in the electrophoresis.

SUMMARY OF THE INVENTION

Thus, in accordance with the present invention, there is provided an enzyme, acyl-CoA synthetase having the following physical and chemical properties:
(i) substrate specificity: acting primarily on straight-chain fatty acids having 14 to 18 carbon atoms and essentially not acting on straight-chain fatty acids more than 18 or less than 14 carbon atoms;
(ii) optimum pH: 7.1–9.6
(iii) pH stability: 6.1–9.0 (at 4° C., 36 hours)
(iv) optimum temperature: 35°–45° C.
(v) thermal stability: 45° C. or below
(vi) activator: $Mg^{++}$
   inhibitor: $Cu^{++}$ and EDTA
(vii) molecular weight:
   approximately 84,000 (by SDS disk electrophoresis)
   approximately 105,000 (by gel filtration)
(viii) amino acid composition: 13.2% lysine, 2.0% histidine, 4.6% arginine, 9.1% aspartic acid, 5.5% threonine, 7.8% serine, 10.5% glutamic acid, 7.5% proline, 8.1% glycine, 6.5% alanine, 6.0% valine, 1.6% methionine, 5.0% isoleucine, 7.0% leucine, 2.9% tyrosine and 2.6% phenylalanine (in molar percentages based on the total amount of the sixteen amino acids). In addition, in accordance with the present invention, there is provided a process for the purification of the enzyme which comprises the steps of: (a) disrupting the enzyme containing microorganism cells to obtain the enzyme which is bound to the membranes, (b) solubilizing the enzyme with a surfactant; and (c) subjecting the solubilized enzyme to affinity chromatography to separate it from contaminant protains.

DETAILED DESCRIPTION OF THE PREFERRED EMBODIMENTS

Further details of the invention will be found in the following description.

The physical and chemical properties of the enzyme, longchain acyl-CoA synthetase, are discussed below in more detail.

Physical and chemical properties of the enzyme (1) Enzyme action:

The enzyme catalyzes the aforementioned reaction (1).

This was demonstrated as follows.

A radioactive water-soluble product obtained by reacting the enzyme with U-14C labeled potassium palmitate as a substrate in the presence of CoA, ATP and $Mg^{++}$ was assayed by TLC and the formation of palmitoyl-CoA was confirmed from the TLC data.

When the above reaction was repeated in the same reaction system except that hydroxylamine was added (the substrate being potassium palmitate), the formation of palmitoylhydroxamic acid was confirmed by silica gel chromatography of the reaction product. From these facts, one of the reaction products was identified as palmitoyl-CoA.

On the other hand, when myokinase was omitted from the standard reaction system used in method 2 for the assay of activity described in paragraph (4) below, no oxidation of NADH took place, indicating that AMP was a reaction product. A stoichiometric relationship at a mole ratio of 1:1 was observed between the amount of palmitic acid or CoA added and that of AMP formed as measured spectrophotometrically as long as the reaction was under such conditions that the amount of palmitic acid or CoA was a limiting factor.

It was confirmed from the above results that acyl-CoA synthetase I catalyzes the above-mentioned reaction (1).

(2) Substrate specificity:

The substrate specificity is reported in Table 1 below. The enzyme specifically utilizes straight-chain fatty acids having 14 to 18 carbon atoms regardless of the degree of unsaturation, while straight-chain fatty acids having more than 18 or less than 14 carbon atoms as well as 16-hydroxypalmitic acid and hexadecanedioic acid are essentially ineffective.

(3) Optimum and stable pH ranges:

The activity of the standard reaction system used in the assay of activity described in paragraph (4) below was assayed in the same way except that the pH was varied with potassium phosphate buffers (pH 6.2 to 7.1), Tris-HCl buffers (pH 7.1 to 8.8) or glycine-NaOH buffers (pH 8.8 to 10.2). As a result, it was found that the enzyme had a broad pH optimum ranging from 7.1 to 9.6.

On the other hand, in order to determine the pH stability of the enzyme, a solution of the enzyme was dialyzed at 4° C. for 36 hours against 0.1 M potassium phosphate buffer solutions (pH 6.1, 7.4, 8.0 and 9.0) containing 2 mM Triton X-100 (a trademark of Rohm and Haas, predominantly comprising isooctylphenyl-polyethoxy alcohol, hereinafter referred to as surfactant T. Surfactant T is presumed to have an average molecular weight of 628.) and 2 mM mercaptoethanol and the activity of the inner solution was then assayed under standard conditions. The results showed that no deactivation of the enzyme occurred at the above pH range.

(4) Assay of activity:

Method 1

The sssay of enzyme activity was carried out by the Banis and Tove method. (See Biochemica et Biophysica Acta, Vol. 348, pages 210–220 (1974)). According to this method, the reaction solution contained 20 μmol of Tris-HCl buffer (pH 7.5), 3 μmol of ATP, 2 μmol of $MgCl_2$, 1.0 μmol of dithiothreitol, 0.2 μmol of [U-14C] potassium palmitate (0.2 mCi/mmol), 0.32 μmol of surfactant T, 0.2 μmol of CoA and an aliquot of the enzyme solution in a total volume of 0.2 ml. After a 5 minute preincubation, either the CoA or the enzyme solution which had been kept from incorporating in the reaction solution was added to initiate the reaction (at 25° C.). At the end of a 10 minute reaction period, 2.5 ml of isopropanol-n-heptane-1 M sulfuric acid (40:10:1) was added to stop the reaction. The solution was then extracted with heptane to remove any unreacted free fatty acid. After the aqueous layer was washed twice each with 2 ml of heptane containing 8 mg of palmitic acid, the radioactivity of the aqueous layer was measured.

The amount of the enzyme which catalyzes the formation of 1 μmol of palmitoyl-CoA per minute under the above-mentioned conditions was defined as one unit (1 U) of activity.

Method 2

The amount of AMP formed in the above-mentioned reaction equation (1) was determined by an enzymatic process as follows.

The standard reaction solution contained 100 μmol of Tris-HCl buffer (pH 7.4), 5 μmol of dithiothreitol, 1.6 μmol of surfactant T, 7.5 μmol of ATP, 10 μmol of $MgCl_2$, 0.25 μmol of potassium oleate, 1 μmol of CoA, 0.2 μmol of potassium phosphoenolpyruvate, 0.15 μmol of NADH, 20 μg of myokinase, 30 μg of pyruvate kinase, 30 μg of lactate dehydrogenase and a certain amount of acyl-CoA synthetase per ml of the solution. A reaction solution containing all the above components except CoA was preincubated at 25° C. for one minute. The reaction was then initiated by the addition of CoA, and the rate of decrease in optical density at 340 nm which was attributed to decrease in amount of NADH was determined.

The amount of the enzyme which catalyzes the formation of 1 μmol of AMP per minute under the above conditions was defined as 1 U of activity. The ratio of the activity determined by method 2 to that determined by method 1 is 1.6.

(5) Optimum temperature range:

The enzyme was reacted at various temperature for 5 minutes using the procedures described in the above method 1. The activity of the enzyme was 190 at 35° C. and 210 at 45° C. as compared with the activity at 25° C. which was arbitrarily designated as 100. Thus, the temperature range optimum for the enzymatic action was from 35° C. to 45° C.

(6) Thermal stability:

After a solution of the enzyme in buffer A (described below) containing 10 mM ATP was kept at various temperatures for 15 minutes, the activity of the enzyme was assayed. When the activity at 25° C. was arbitrarily designated as 100, those at 35° C., 45° C. and 52° C. were 100, 100 and 55, respectively.

(7) Activator and inhibitor:

The enzyme is activated with $Mg^{++}$, while $Cu^{++}$ ion, at a concentration of 15 mM, completely inhibits the enzyme action and EDTA also inhibits it.

(8) Purification process:

The enzyme was isolated and purified generally as follows:

From the homogenate resulting from disrupture of microorganism cells, the particulate fraction is isolated by ultracentrifugation and treated with surfactant T to liberate the enzyme from the membranes. Subsequently, the resulting enzyme-containing solution is successively subjected to cation-exchange chromatography on phosphocellulose, demineralization and affinity chromatography (for example, on Blue Sepharose CL-6B, a trademark of Pharmacia Fine Chemicals). Elution of the affinity chromatography column is carried out at an ATP concentration of 10 mM and at NaCl gradient concentration varying from 0 to 1.5 M, followed by demineralization and gel filtration with a column of Sephadex G-100 (a trademark of Pharmacia Fine Chemicals). Further details will be found in the preparation example described below.

(9) Molecular weight:

The molecular weight was determined with a solution of the enzyme containing 2 mM surfactant T. The molecular weight determined from the electrophoretic mobility of the enzyme treated with sodium dodecylsulfate and 2 mercaptoethanol was 84,000 (Rf=0.4), while that determined by gel filtration using Sephadex G-200 was 105,000. It is thought that this difference results from binding of a considerable portion of surfactant T to the enzyme.

(10) Analysis of amino acid components:

After the enzyme was degraded with 6 N hydrochloric acid at 110° C. for 20 hours, the amino acids were assayed. The results are as follows:

13.2% lysine, 2.0% histidine, 4.6% arginine, 9.1% aspartic acid, 5.5% threonine, 7.8% serine, 10.5% glutamic acid, 7.5% proline, 8.1% glycine, 6.5% alanine, 6.0% valine, 1.6% methionine, 5.0% isoleucine, 7.0% leucine, 2.9% tyrosine and 2.6% phenylalanine.

The above values are molar percentage based on the total amount of the above sixteen amino acids in which the value of serine was corrected for 10% breakdown and those of threonine and tyrosine were for 5% breakdown.

(11) Crystal structure:

The crystal structure of the enzyme is not known since it has not been obtained in crystalline form.

(12) Other properties:

(i) Specificity for acyl acceptors:

The Vmax values and the apparent Km values were as follows:

| Acyl acceptor | Vmax | Km (mM) |
|---|---|---|
| CoA | designated as 100% | 0.042 |
| Dephospho-CoA | 70% | 0.11 |
| 1:$^6$N-Etheno-CoA | 40% | 0.5 |
| 4'-Phosphopantetheine | 63% | 3.3 |
| Pantetheine | 57% | 2.5 |
| N-Acetylcysteamine | Not utilized at conc. up to 5 mM | |
| L-Cysteine | Not utilized at conc. up to 5 mM | |
| Glutathione | Not utilized at conc. up to 5 mM | |
| Dithiothreitol | Not utilized at conc. up to 5 mM | |

(ii) Specificity for nucleoside-5'-triphosphate: Only ATP and αATP were effective. At concentrations of 7.5 mM and 15 mM, the activities measured with αATP were 78% and 61%, respectively, of those measured with ATP. At the same concentrations, GTP, UTP, CTP, αTTP, adenylyl (β,γ-methylene)diphosphonate and adenylyl imidodiphosphonate were essentially ineffective.

Figure 1:
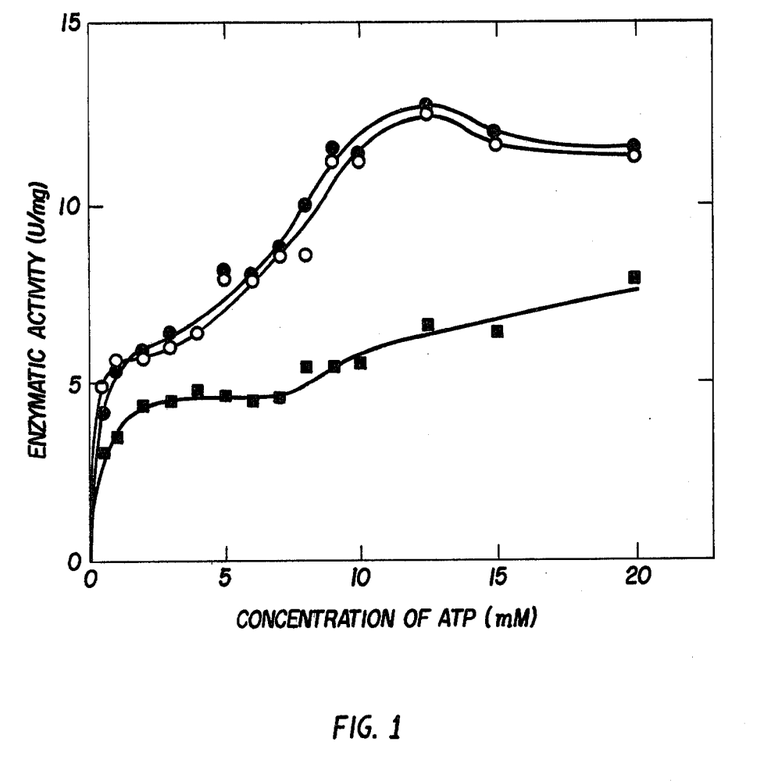
FIG. 1 illustrates the relationship of the ATP concentration (mM) on the abscissa and the activity of acyl-CoA synthetase (U/mg protein) on the ordinate in the presence of $Mg^{++}$ at concentrations of 5 mM (○), 10 mM (●) and 15 mM (■)

The relationship between the concentration of ATP and the activity of acyl-CoA synthetase in the presence of a predetermined amount of $M^{++}$ ion is shown in FIG. 1.

TABLE 1

Substrate specificity of acyl-CoA synthetase

| Fatty acid | Concentration (mM) | Activity (μmol acyl-CoA/min.) |
|---|---|---|
| Lauric acid | 0.25 | 1.0 |
| Tridecanoic acid | 0.125 | 1.3 |
| Myristic acid | 0.25 | 20.8 |
| Pentadecanoic acid | 0.25 | 18.0 |
| Palmitic acid | 0.25 | 20.4 |
| Heptadecanoic acid | 0.125 | 22.3 |
| Stearic acid | 0.125 | 11.3 |
| Nonadecanoic acid | 0.25 | 1.7 |
| Arachidic acid | 0.25 | 0.6 |
| Palmitoleic acid | 0.125 | 19.8 |
| Oleic acid | 0.25 | 23.8 |
| Linoleic acid | 0.25 | 19.7 |
| Linolenic acid | 0.25 | 22.0 |
| Arachidonic acid | 0.125 | 1.3 |
| 16-Hydroxypalmitic acid | 0.25 | 1.5 |
| Hexadecanedioic acid | 0.25 | 0.6 |

When compared to the known acyl-CoA synthetase, for example, that of animal origin as described in the aforementioned paper by J. Bar-Tana et al and in "Methods in Enzymology", edited by J. M. Lowenstein, Academic Press (1975), Vol. 35, pages 117–122, the enzyme of this invention is apparently different in molecular weight, optimum pH and substrate specificity. Thus, it is believed that the two enzymes are entirely distinct from each other.

The enzyme of this invention can be prepared in pure form according to the process described below in detail.

The microorganisms that are used in the preparation of the enzyme is not critical and may be any of those microorganisms which contain in their cells long-chain acyl-CoA synthetase produced consitutively or inductively. The enzyme occurs in a wide variety of microorganisms, from which it can be extracted and purified. Among others, those microorganisms which grow rapidly, have a high activity of the enzyme and are readily extractable are preferred from a commercial standpoint. Such microorganisms are exemplified by yeasts and bacteria.

Examples of preferred microorganisms are yeasts belonging to Candida or Saccharomyces and bacteria belonging to Escherichia, Bacillus or Pseudomonas. More specifically, the preferred microorganisms include yeast strains belonging to *Candida lipolytica, Candida tropicalis* and *Saccharomyces cerevisiae* and bacterium strains belonging to *Escherichia coli* and *Bacillus megaterium*. Among these, the most preferred are *Candida lipolytica* strain NRRL Y-6795 selected from *Candida lipolytica* and a commercially available baker's yeast from *Saccharomyces cerevisiae.*

The method for the cultivation of these microorganisms is not critical and may be conducted on any conventional medium containing sources of carbon (e.g., glucose) and nitrogen, phosphate, potassium, magnesium, etc., under normal culture conditions of temperature and period. When the microorganisms used produce the enzyme inductively, an inducer substance (e.g., a fatty acid) may be added to the medium.

The cultivated microorganism cells are collected by means of centrifugation, filtration or the like. The cells are then disrupted by a mechanical means such as homogenizer, ultrasonic treatment or glass bead milling or a chemical means such as treatment with a cell wall resolving enzyme, and fragments of the cells are removed by centrifugation.

The separated supernatant which contains the particulate fraction of the cells is then treated with a surfactant to liberate the enzyme from the particles. Alternatively, prior to this treatment, the supernatant may be ultracentrifuged in order to precipitate the particulate fraction, which is then suspended in an appropriate buffer solution and treated with a surfactant.

The surfactants that are used include bile acids such as sodium cholate and sodium deoxycholate; and non-ionic surfactants such as polyoxyethylene alkyl ethers, polyoxyethylene alkylphenol ethers, polyoxyethylene alkyl esters, sorbitan alkyl esters and polyoxyethylene sorbitan alkyl esters. Among these, non-ionic surfactants, for example, polyoxyethylene alkylphenol ethers are preferred with the above-mentioned surfactant T being most preferred.

The amount of surfactant used is usually in the range of 0.1 to 1.0 w/v% depending on the particular microorganisms and surfactant used.

The solubilization treatment of the enzyme with a surfactant is typically carried out for 0.5 to 2 hours at a relatively low temperature, for example, at 0° to 10° C., preferably at 0° to 4° C. In order to prevent deactivation of the enzyme which may possibly take place along with the solubilization, a phosphate buffer, a protective agent for the enzyme such as mercaptoethanol, EDTA and other appropriate additives may be added to the suspension to be treated.

After the enzyme has been solubilized under these conditions, the suspension is ultracentrifuged to separate the enzyme now contained in the supernatant from the particulate fraction. The supernatant is then purified by affinity chromatography. Preferably the supernatant may be pretreated by another appropriate purification procedure prior to affinity chromatography.

One of such procedures is ion-exchange chromatography on phosphocellulose, whereby anionic proteins and other contaminants can be removed. In the procedure of phosphocellulose column chromatography, the enzyme is usually eluted from the column with a phosphate buffer solution, and in this case the eluate is preferably demineralized prior to the next step of affinity chromatography.

Subsequently the enzyme-containing solution is purified by affinity chromatography. The adsorbent used in this procedure should be selected to adsorb selectively those enzymes having affinity for ADP, ATP, CoA and similar substances. Thus, the structure of the adsorbent should contain as a ligand a moiety which is structurally analogous to ADP, ATP and/or Coa. By the expression "structurally analogous" used herein is meant that the ligand has an affinity and a selective adsorptivity for those enzymes which catalyze ADP, ATP and/or CoA-participating reactions.

Examples of such ligand substances structurally analogous to ADP, ATP and/or CoA are disodium 1-amino-4-(4'-aminophenylamino)-anthraquinone-2,3'-disulfanate of the formula:

and a compound of the formula:

wherein one of $R^1$ and $R^2$ is hydrogen and the other is —$SO_3Na$ radical. The compound of formula (I) is available from Ciba Geigy under the tradename of Cibacron Blue F3G-A (this product being hereinafter referred to as ligand C).

For the purpose of purification of the enzyme, the adsorbent used in affinity chromatography preferably contains either of these ligand bound to a support in such a way that the structural analogousness of the ligand is not impaired. No spacer is required, but it may be inserted if desired.

The support for the above ligand is not critical, but a polysaccharide or porous glass is desirable for the support because of its large pore size and high mechanical strength, mild conditions required in binding the ligand thereto and little non-selective adsorption of proteins thereon. Particularly preferable polysaccharides are dextran, agarose and their cross-linked products and these polysaccharides in the form of beads are easily handled.

The most preferred adsorbent useful for the affinity chromatography step is a substance represented by the formula:

wherein one of $R^1$ and $R^2$ is hydrogen and the other is —$SO_3Na$ radical; and X is a polysaccharide residue. An example of this type of adsorbent commercially available is Blue-Sepharose CL-6B (a trademark of Pharmacia Fine Chemicals; hereinafter referred to as B.S.), which consists of the above-mentioned ligand C as the ligand and Sepharose CL-6B (a trademark of Pharmacia Fine Chemicals, predominantly composed of cross-linked agarose) as the support.

In practice of affinity chromatography, the above-mentioned enzyme-containing solution is applied to a column packed with the affinity adsorbent as above to effect adsorption. Thereafter a buffer solution containing ATP, ADP, AMP, CoA and the like is passed through the column to wash out some proteins, and these protein-containing fractions exhibit no activity. The column is then treated with a solution for gradient elution which contains sodium chloride in the above ATP-containing buffer solution to provide a gradient condition varying from 0 to 1.5 M NaCl. During the gradient elution additional proteins are eluted separately from the column and the enzyme is eluted in a single peak in the fractions at an NaCl concentration range of 0.05 to 0.5 M.

It is presumed from the above results that the chromatograhic isolation of the enzyme in this column is partly attributable to ion-exchange phenomenon in addition to the affinity of the adsorbent.

The enzyme solution thus obtained has a considerably high specific activity. However, it may be further purified, when necessary. Suitable means for the further purification of the enzyme are typically treatment with Sephadex G-100 (a trademark of Pharmacia Fine Chemicals; hereinafter referred to as G-100) and subsequent hydroxyapatite chromatography.

The acyl-CoA synthetase purified as above is of extremely high purity and gives a single band in an SDS electrophoretic test.

An essential feature of the above process for purification of the enzyme is a combination of solubilization of the enzyme with a surfactant in order to liberate it from the membranes and affinity chromatography in order to isolate it from other contaminant proteins. None of the prior art processes have utilized affinity chromatography for the purpose of purifying acyl-CoA synthetase. It has now been found that affinity chromatography can be applied to purification of the enzyme very successfully.

In the prior art processes for the purification of acyl-CoA synthetase, it has been proposed to solubilize the enzyme with surface-active deoxycholic acid. However, when the solubilization treatment is followed by conventional purification procedures such as salting-out with ammonium sulfate, ion-exchange chromatography and the like, it was found that the quality of the purified enzyme was not satisfactory in terms of purity and specific activity. Surprisingly, it has now been found that the solubilization treatment with the above-mentioned surfactant, when combined with affinity chromatographic purification, results in isolation of the enzyme in highly pure form with ease.

In recent years affinity chromatography has been widely applied to purification of enzymes and gradually employed in the purification of those enzymes participating in lipid metabolism. However, to the inventors' knowledge, nobody had attempted to purify the enzyme, acyl-CoA synthetase, by means of affinity chromatography before the inventors made this attempt. As a result of the attempt, the inventors have found that the enzyme can be very readily separated by affinity chromatography from the other proteins including such proteins as ATPase which have similar physical properties and hence are difficult to remove from acyl-CoA synthetase by conventional purification procedures.

It is a feature of the process that the enzyme is derived from microorganisms. When it is desired to readily and inexpensively obtain a large amount of an enzyme, microorganisms are quite excellent sources. For this reason, the present invention provides a process for the commercialscale production of acyl-CoA synthetase.

Another feature of the process is that the purified enzyme is of high purity and has an extremely high specific activity on the order of approximately 50 to 100 times higher than that of the prior art one. More specifically, the above-mentioned acyl-CoA synthetase from E. coli, even in the most purified form, could not be regarded as homogeneous in electrophoresis and had a specific activity as low as 106 mU/mg protein, and the enzyme purified from the rat liver had a specific activity of 250 mU/mg protein. On the contrary, the enzyme from *Candida lipolytica* purified in accordance with the invention is entirely homogeneous in electrophoresis and brings about a 50 to 100-fold increase in specific activity.

As shown in the foregoing reaction equation, the enzyme utilizes free fatty acids and thus liberates AMP in an amount equivalent to that of the free fatty acids. Therefore, concentration of free fatty acids in blood can be assayed by an enzymatic process through assay of the liberated AMP using the following reaction system (see Rinsho Kagaku, Vol. 2, No. 2, page 179 (1975), Nippon Rinsho Kenkyukai, Japan):

Thus, the enzyme of the invention functions very satisfactorily as a diagnostic enzyme for use in assay of free fatty acids in blood.

The enzyme is also useful for the preparation of a labeled acyl-CoA that is an important biochemical reagent. This reagent can be prepared advantageously from a labeled fatty acid using the enzyme.

Having generally described this invention, a more complete understanding can be obtained by reference to certain preparation and reference examples which are provided herein for purpose of illustration only and are not intended to be limiting in any manner.

Preparation

Candida lipolytica strain NRRL Y-6795 was shaken cultured in twenty-four 2-liter flasks each containing 500 ml of a medium of pH 5.2 which contains 2% glucose, 0.5% $NH_4H_2PO_4$, 0.25% $KH_2PO_4$, 0.1% $MgSO_4.7H_2O$, 0.002% $FeCl_3.6H_2O$ and 0.1% Bact yeast extract (Difco, U.S.A.). The incubation temperature was 25° C. and the shaking speed was 72 reciprocations per minute. The yeast cells were harvested at the mid-logarithmic growth phase by centrifugation and thus 250 g of the wet yeast cells were obtained.

Subsequently, the yeast cells were washed with 0.1 M phosphate buffer solution (pH 6.5), then suspended in the same phosphate buffer solution containing 5 mM 2-mercaptoethanol and 1 mM EDTA, and disrupted with a Braun cell homogenizer (Melsungen, F. R. G.) under cooling with liquid $CO_2$ (hereinafter all the procedures being conducted at a temperature of 0° to 4° C.).

The resulting homogenate was centrifuged at 8,000 G for 15 to 20 minutes in order to collect the supernatant fraction, which was then ultracentrifuged at 230,000 G for an hour in order to collect the precipitation fraction. This fraction (hereinafter referred to as particulate fraction) was suspended in the same phosphate buffer solution as above containing 2-mercaptoethanol and EDTA at the same concentrations to give a total amount of 72 ml of a suspension having a protein concentration of 46 mg/ml.

The suspension was then admixed with a solution containing surfactant T, a phosphate buffer pH 7.4, 2-mercaptoethanol and EDTA, the final concentrations of which in the mixture were 5 mM, 50 mM, 5 mM and 0.5 mM, respectively, to give a protein concentration of 11 mg/ml. The mixture was allowed to stand for an hour and then ultracentrifuged at 230,000 G for an hour. The resulting supernatant amounting to 265 ml was collected.

After the supernatant was diluted with 1.5 volumes of an aqueous solution containing 2 mM surfactant T and 5 mM 2-mercaptoethanol, the diluted solution was passed through a 52 mm ×75 mm column of Phosphocellulose P-11 ( a trademark of Whatman) which had been equilibrated with 20 mM phosphate buffer solution containing 20 mM surfactant T and 5 mM 2-mercaptoethanol (this solution being hereinafter referred to as buffer solution A). After the adsorbent column was washed with 2 column volumes of buffer solution A, gradient elution was carried out with an eluent in which a linear concentration gradient was established between 2.5 column volumes of buffer solution A and the same volume of 0.5 M phosphate buffer solution (pH 7.4) containing 2 mM surfactant T and 5 mM mercaptoethanol. The flow rate in the elution was about 90 ml/hr. and each 15 ml fraction was collected. Since the desired enzyme appeared in a single peak at a phosphate concentration range between 0.05 M and 0.15 M, the fractions exhibiting specific activities of 0.28 U/mg or higher were isolated and combined (90 ml).

Next, for the purpose of demineralization, the combined fractions were passed through a 38 mm × 350 mm column of Sephadex G-50 (a trademark of Pharmacia Fine Chemicals) which had been equilibrated with buffer solution A and all the protein-containing fractions emerged from the column were combined.

Figure 2:
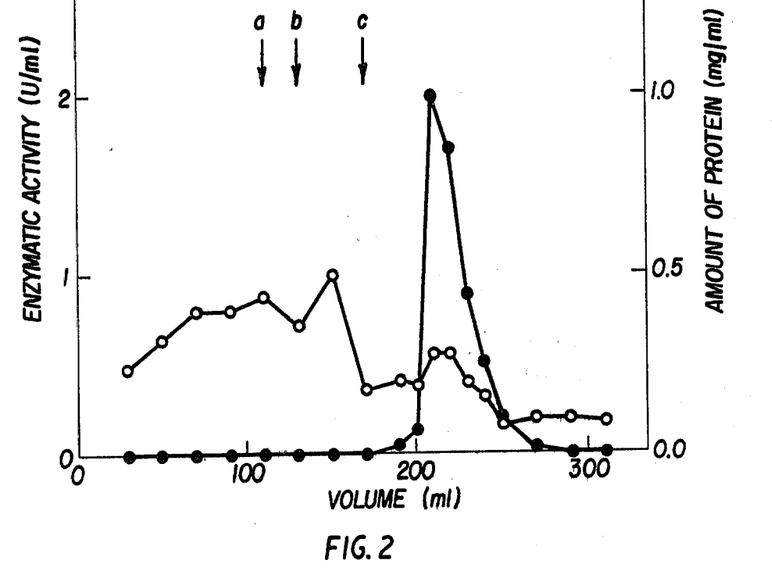
FIG. 2 illustrates the elution of acyl-CoA synthetase from the B. S. column in the preparation example. The abscissa indicates the volume of the effluent (ml); the ordinate indicates the activity of acyl-CoA synthetase (U/ml, on the left hand) plotted by ● and the amount of proteins (mg/ml, on the right hand) plotted by ○; and the arrows a–c indicate that (a) buffer A was applied to the column at arrow a, (b) buffer A containing 10 mM ATP was applied at arrow b and (c) the gradient elution was started at arrow c.

The combined fractions were then applied to a B.S. column (16 mm × 100 mm) which had been equilibrated with buffer solution A. After the column was washed with one column volume of buffer solution A and then with 2 column volumes of buffer solution A containing 10 mM ATP, gradient elution was carried out at a flow rate of 30 ml/hr. under a linear concentration gradient condition established between 3.75 column volumes of buffer solution A and the same volumes of buffer solution A containing 1.5 M NaCl, and each 10 ml fraction was collected. The elution profile is shown in FIG. 2. During this elution, the desired enzyme emerged from the column in a single peak at an NaCl concentration range between 0.1 M and 0.3 M. The fractions having specific activities of 2.6 U/mg or higher were isolated and combined (50 ml).

The combined fractions were concentrated to 10 ml by ultrafiltration with Diaflo membrane filter PM-30 (Amicon Far East, Tokyo, Japan) and then applied to a G-100 column (27 mm×870 mm) equilibrated with buffer solution A.

Figure 3:
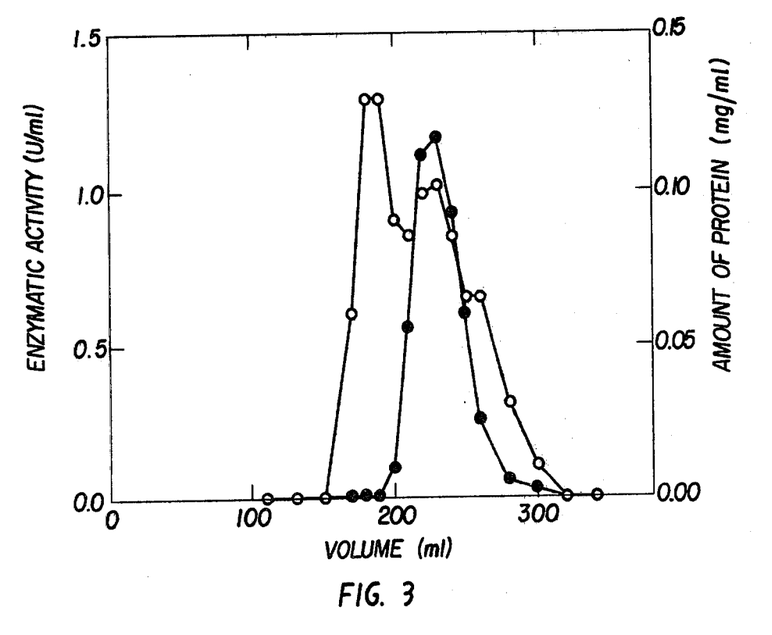
FIG. 3 illustrates the elution of acyl-CoA synthetase in the preparation. The abscissa indicates the volume of the effluent (ml) and the ordinate indicates the activity of acyl-CoA synthetase (U/ml, on the left hand) plotted by ● and the amount of proteins (mg/ml, on the right hand) plotted by ○.

Thereafter the column was eluted with buffer solution A at a flow rate of 30 ml/hr. and each 10 ml fraction was collected. The elution profile is shown in FIG. 3. The enzyme activity was in coincidence with the second protein peak. The fractions having specific activities of at least 9 U/mg were isolated and combined (40 ml).

The following Table 2 summarizes the data obtained at various purification stages in this preparation.

TABLE 2

| Fraction | Protein* (mg) | Total activity (U) | Specific activity (U/mg) | Yield (%) |
| --- | --- | --- | --- | --- |
| Particulate fraction | 3,312 | 311 | 0.094 | 100 |
| Supernatant after solubilization | 1,574 | 238 | 0.151 | 77 |
| Phosphocellulose treated | 96.0 | 63.8 | 0.665 | 21 |
| B.S. treated | 10.1 | 54.8 | 5.43 | 18 |
| G-100 treated | 3.5 | 37.8 | 10.8 | 12 |

*The amount of proteins was assayed in accordance with the Lowry method.

Figure 4A:
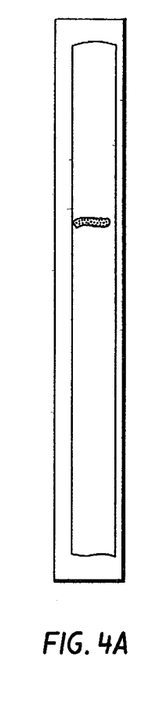
FIG. 4 shows a polyacrylamide gel electrophoretic pattern of acyl-CoA synthetase in the presence (A) of or absence (B) of sodium dodecylsulfate.
Figure 4B:
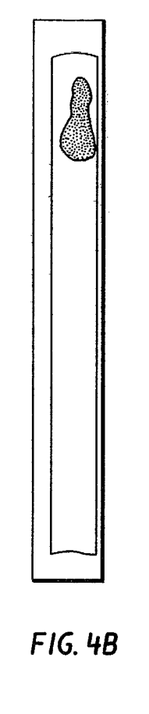

The homogeneity of the acyl-CoA synthetase purified by the above-mentioned process is evident from its polyacrylamide gel electrophoretic pattern (FIG. 4). In addition, it was immunochemically evidenced that the purified enzyme in this preparation which was derived from glucose-grown cells is indistinguishable from acyl-CoA synthetase I derived from the same yeast strain grown on a medium containing as the carbon source oleic acid in place of glucose, but distinguishable from acyl-CoA synthetase II which participates in the $\beta$-oxidation systems of fatty acids.

REFERENCE EXAMPLE 1

In this example, variation in amount of a fatty acid was determined in the presence of the acyl-CoA synthetase purified as described in the preparation example.

Figure 5:
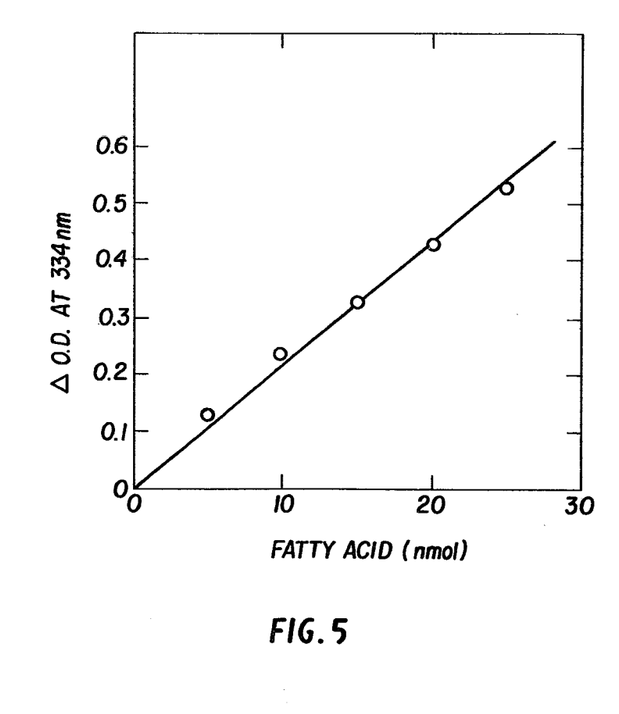
FIG. 5 illustrates the relationship between the amount of a fatty acid (nmol) on the abscissa and the ΔO.D. value at 334 nm on the ordinate obtained in Reference Example 1.

A reaction solution containing a predetermined amount of potassium oleate, 100 $\mu$mol of Tris-HCl buffer pH 7.4, 5 $\mu$mol of dithiothreitol, 1.6 $\mu$mol of surfactant T, 7.5 $\mu$mol of ATP, $\mu$mol of MgCl$_2$, 0.2 $\mu$mol of potassium phosphoenolpyruvate, 0.15 $\mu$mol of NADH, 20 $\mu$g of myokinase, 30 $\mu$g of pyruvate kinase, 30 $\mu$g of lactate dehydrogenase and 4 $\mu$g of the purified acyl-CoA synthetase per ml of the solution was placed in a cell of a spectrophotometer (Eppendorf, model 1101M) and preincubated at 25° C. for a minute. A solution containing 0.5 $\mu$mol of CoA in a total volume of 0.5 ml was then added to initiate the reaction, the variation in optical density (O.D.) at 334 nm which was attributed to decrease in amount of NADH was read from the chart on the recorder. As shown in FIG. 5, a good linear relationship was observed between the amount of potassium oleate in the solution and the $\Delta$O.D. value at 334 nm as long as the amount of oleic acid was in the range of 0 to 25 nmol.

REFERENCE EXAMPLE 2

Using 10 nmol of various long-chain fatty acids, the $\Delta$O.D. values were determined in the same way as described in Reference Example 1.

The results are summarized in Table 3. It can been seen from Table 3 that the experimental data obtained in this example are in good coincidence with the theoretical value, 0.246, of $\Delta$O.D. at 334 nm given by H. U. Bergmeyer in Zeitschrift für Klinische Chemie and Klinische Biochemie, Vol. 13, pages 507–508 (1975).

TABLE 3

| Fatty acid | ΔO.D. at 334 nm |
|---|---|
| Myristic acid | 0.210 |
| Palmitic acid | 0.245 |
| Palmitoleic acid | 0.235 |
| Stearic acid | 0.230* |
| Oleic acid | 0.240 |
| Linoleic acid | 0.240 |
| Linolenic acid | 0.250 |

*Reaction period was 20 minutes.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for the purification of a long-chain acyl CoA synthetase derived from microorganisms which comprises:

disrupting microorganism cells containing long-chain acyl CoA synthetase to obtain the enzyme which is bound to the membranes and then solubilizing the enzyme with a surfactant; and subjecting the solubilized enzyme to affinity chromatography using a ligand which is a structural analog selected from the group consisting of ADP, ATP, CoA, and mixtures thereof, to separate it from contaminant proteins.

2. The process according to claim 1, wherein the microorganisms are selected from the group consisting of yeasts and bacteria.

3. The process according to claim 1, wherein the ligand is a substance represented by the formula:

in which one of $R^1$ and $R^2$ is hydrogen and the other is —$SO_3$ Na radical.

4. The process according to claim 1 wherein the adsorbent used in the affinity chromatography is a substance represented by the formula:

in which one of $R^1$ or $R^2$ is hydrogen, the other is —$SO_3Na$ radical; and X is a polysaccharide residue.

5. A process for the purification of long-chain acyl CoA synthetase, having the following physical and chemical properties:

(i) substrate specificity: acting primarily on straight-chain fatty acids having 14 to 18 carbon atoms and essentially not acting on straight-chain fatty acids more than 18 or less than 14 carbon atoms;

(ii) optimum pH: 7.1–9.6
(iii) pH stability: 6.1–9.0 (at 4° C., 36 hours)
(iv) optimum temperature: 35°–45° C.
(v) thermal stability: 45° C. or below
(vi)
   activator: Mg++
   inhibitor: Cu++ and EDTA
(vii)
   molecular weight: approximately 84,000 (by SDS disk electrophoresis);
   approximately 105,000 (by gel filtration)
(viii) amino acid composition: 13.2% lysine, 2.0% histidine, 4.6% arginine, 9.1% aspartic acid, 5.5% threonine, 7.8% serine, 10.5% glutamic acid, 7.5% proline, 8.1% glycine, 6.5% alanine, 6.0% valine, 1.6% methionine, 5.0% isoleucine, 7.0% leucine, 2.9% tyrosine and 2.6% phenylalanine (in molar percentages based on the total amount of the sixteen amino acids)

comprising the steps of:

disrupting microorganism cells containing long-chain acyl-CoA synthetase to obtain the enzyme which is bound to the membranes and then solubilizng the enzyme with a surfactant; and subjecting the solubilized enzyme to affinity chromatography using a ligand therefor which is a structural analog of a compound selected from the group consisting of ADP, ATP, CoA, and mixtures thereof, to separate said enzyme from contaminant proteins.

6. The process according to claim 5 wherein the microorganisms are selected from the group consisting of yeasts and bacteria.

7. The process according to claim 6 wherein the microorganisms are bacteria selected from the group consisting of Escherichia, Bacillus and Pseudomonas.

8. The process according to claim 6 wherein the microorganisms are yeasts selected from the group consisting of Candida and Saccharomyces.

9. The process according to claim 5 wherein the ligand is a a substance represented by the formula:

(I)

in which one of $R^1$ and $R^2$ is hydrogen and the other is —$SO_3Na$ radical.

10. The process according to claim 5 wherein the adsorbent used in the affinity chromatography is a substance represented by the formula:

(II)

in which one of $R^1$ and $R^2$ is hydrogen, the other is —$SO_3Na$ radical; and X is a polysaccharide residue.

* * * * *